United States Patent [19]

Shepherd

[11] 4,311,846

[45] Jan. 19, 1982

[54] 4-[(MONOSUBSTITUTED-ALKYL) AMINO]BENZOIC ACIDS AND ANALOGS AS HYPOLIPIDEMIC AND ANTIATHEROSCLEROTIC AGENTS

[75] Inventor: Robert G. Shepherd, South Nyack, N.Y.

[73] Assignee: American Cyanamid Company, Stamford, Conn.

[21] Appl. No.: 176,890

[22] Filed: Aug. 11, 1980

Related U.S. Application Data

[62] Division of Ser. No. 881,456, Feb. 27, 1978, Pat. No. 4,245,097.

[51] Int. Cl.$^3$ ............... C07C 103/78; C07C 103/84; C07D 211/32
[52] U.S. Cl. .................... 546/226; 260/239 A; 260/239 B; 260/326.5 J; 260/507 R; 548/201; 562/442; 562/450; 562/451; 564/99; 564/149; 564/157; 564/163

[58] Field of Search ............... 260/349, 239 A, 239 B, 260/326.5 J, 507 R; 546/226; 548/201; 562/442, 450, 451; 564/99, 149, 157, 163

[56] References Cited

U.S. PATENT DOCUMENTS

| 3,787,478 | 1/1974 | Dolejs et al. | 260/340.5 R X |
|---|---|---|---|
| 3,868,416 | 2/1975 | Albright et al. | 525/310 |
| 4,036,977 | 7/1977 | Lednicer | 260/326.5 X |
| 4,245,097 | 1/1981 | Shepherd | 546/245 |

OTHER PUBLICATIONS

Chemical Abstracts, Seventh Collective Index, vols. 56-65, Subjects Amn-Be, p. 3067 S, (ACS).
Chemical Abstracts Ninth Collective Index, 1,3-Benzenediol-Benzenitrile Methoxy, p. 6359 CS, copyrighted 1978 ACS.

*Primary Examiner*—Richard Raymond
*Attorney, Agent, or Firm*—Robert P. Raymond

[57] ABSTRACT

This disclosure describes novel 4-[(monosubstituted-alkyl)amino]benzoic acids and analogs which are useful as hypolipidemic and antiatherosclerotic agents.

6 Claims, No Drawings

4-[(MONOSUBSTITUTED-ALKYL)AMINO]BENZOIC ACIDS AND ANALOGS AS HYPOLIPIDEMIC AND ANTIATHEROSCLEROTIC AGENTS

This is a division of application Ser. No. 881,456 filed Feb. 27, 1978, now U.S. Pat. No. 4,245,097.

BRIEF SUMMARY OF THE INVENTION

This invention relates to new organic compounds and, more particularly, is concerned with 4-[(monosubstituted-alkyl)amino]benzoic acids and analogs which may be represented by the following structural formula:

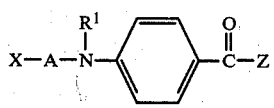

wherein

X is selected from the group consisting of mercapto, loweralkylthio, aralkylthio, arylthio, loweralkylsulfinyl, loweralkylsulfonyl, aralkylsulfinyl, aralkylsulfonyl, arylsulfinyl, arylsulfonyl, arylamino, acylamino, loweralkylsulfonylamino, arylsulfonylamino, azido, oxo, oximino, chloro, bromo, and iodo;

wherein the substituent X may contain q carbon atoms with q being an integer from 0 to 8, inclusive;

A is an unbranched or branched alkylene group, optionally saturated or (mono- or poly-)unsaturated and containing or not containing a cycloalkyl group, represented by the formula $C_nH_{2(n-p)}$ with n being an integer from 7 to 18, inclusive, and p being an integer from 0 to 5, inclusive, both being selected in a manner such that the sum of n and q is greater than 6 but less than 19;

with the proviso that when X is halogen A must be a saturated alkylene group;

and Z is selected from the group consisting of hydrogen, hydroxy, loweralkoxy, loweralkoxyloweralkoxy, diloweralkylaminoloweralkoxy, (mono- or polyhydroxy)loweralkoxy, allyloxy, 2,3-epoxypropoxy, substituted or unsubstituted (benzyloxy, phenoxy, or pyridylmethoxy), 3-pyridyloxy, mono- or poly-carboxy(loweralkoxy or hydroxyloweralkoxy), tetrahydropyranyloxy, (mono- or polyhydroxy)alkylamino, allylamino, propargylamino, 2-sulfoethylamino, (mono- or polycarboxyl)loweralkylamino, loweralkanoylamino, (substituted or unsubstituted aroyl)amino, loweralkanesulfonylamino, (substituted or unsubstituted arene)sulfonylamino, loweralkanoylhydrazino, hydroxylamino, polymethyleneimino, and 4-carboethoxy- or 4-carboxythiazolidino;

wherein $R_1$ is hydrogen or is a group convertible in vivo thereinto such as, most notably, methyl, ethyl, carboxymethyl, acetyl, trifluoroacetyl, succinyl, 1-(sodium sulfo)loweralkyl, 1-(sodium sulfo)polyhydroxyalkyl, and 1,3-bis(sodium sulfo)aralkyl;

and the pharmaceutically acceptable non-toxic acid addition and cationic salts thereof.

The loweralkyl, loweralkoxy, loweralkanoyl, loweralkylthio, loweralkanesulfinyl, and loweralkanesulfonyl groups herein contain 1 to 6 carbon atoms and may be branched or unbranched. The number of hydroxyl groups in the polyhydroxy compounds herein are from 2 to 4 hydroxy groups. The number of carbonyl groups in the polycarboxy compounds herein are from 2 to 4 carboxyl groups.

Suitable groups contemplated by the present invention for the substituent X, are for example, methylthio, n-butylthio, benzylthio, p-chlorobenzylsufinyl, p-methylbenzyl(sulfonyl, p-fluorophenylsulfonyl, phenylsulfonyl, p-chlorophenylamino, phenylamino, acetamido, benzamido, methanesulfonamino, p-toluenesulfonamido, and the like.

Suitable alkylene, alkenylene, alkynylene, and cycloalkylene groups contemplated by the present invention for the moiety A are, for example, octamethylene, undecamethylene, tetradecamethylene, hexadecamethylene, 3-methylheptamethylene, 1,1,6-trimethylheptamethylene, 1-(n-butyl)pentamethylene, 1-ethyl-1-methylpentamethylene, 2,7-dimethyloctamethylene, 1-(n-octyl)decamethylene, 2-undecenylene, 1-(2-butenyl)decamethylene, 1-(1-methyl-2-propenyl)decamethylene, 1-(n-hexyl)-3-decenylene, 7-hexadecenylene, 9-hexadecenylene, 1-(n-butyl)-3-dodecenylene, 12-hexadecenylene, 3,7,7-trimethyl-2-heptenylene, 1-(n-propyl)-2-heptenylene, 2-decenylene, 9-methyl-2-nonenylene, 1-(n-pentyl)-2-undecynylene, 1-ethyl-2-tridecynylene, 1-(n-hexyl)-4-decynylene, 4-hexadecynylene, 2,6,6-trimethyl-1,3-cyclohexylenemethylene, 2,2,4-trimethyl-1,3-cyclopentylenemethylene, and the like.

Suitable groups contemplated by the present invention for the substituent Z are, for example, methoxy, isopropoxy, 2-ethoxyethoxy, 2-dimethylaminoethoxy, 1-methyl-4-piperidyloxy, 4-pyridylmethoxy, 2,3-dihydroxypropoxy, 2-hydroxypropoxy, 3-hydroxypropoxy, 4-chlorobenzyloxy, 3-methylbenzyloxy, 4-fluorophenoxy, 4-sulfophenoxy, 2,6-dichlorophenoxy, 3-carboxyphenoxy, 2,6-dimethyl-3-pyridyloxy, 6-methoxy-3-pyridyloxy, 2-hydroxy-3-pyridyloxy, 5-carboxy-3-pyridyloxy, carboxymethoxy, 1-methoxycarbonylpropoxy, 2-methoxycarbonyl-2-propoxy, 2,3-dihydroxypropylamino, carboxymethylamino, acetylamino, benzoylamino, 4-chlorobenzoylamino, methanesulfonylamino, p-toluenesulfonylamino, 1-piperidyl, and the like.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-[monosubstituted-alkyl)amino]benzoyl compounds of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said compounds.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, lagely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart diseases or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [Levy and Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds of this invention are new and novel mono-substituted derivatives of the alkyl moiety of the 4-alkylaminobenzoic acids described in U.S. Pat. No. 3,868,416 and novel esters and amides thereof, and have therapeutically useful biological and pharmacological properties. No hypolipemic activity has been reported in the literature for these compounds and they are different in structure and superior in action to other hypolipidemic agents. The compounds of this invention lower serum-lipid concentrations and also decrease the deposition of lipids in the aorta. The novel compounds of this invention are reliably absorbed from the gastrointestinal tract and cause little, if any gastrointestinal irritation.

We have now found that certain members of this class of compound can safely and effectively lower both serum sterols and triglycerides in warm-blooded mammals. Such actions on serum-lipid components are considered to be very useful in the treatment of atherosclerosis, especially in contrast to available drugs whose action is much more limited. For some time it has been considered important to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The 4-[(monosubstituted-alkyl)amino]benzoic acids and analogs of the present invention are, in general, white crystalline solids having characteristic melting points and absorption spectra. They are soluble in organic solvents such as lower alkanols, chloroform, toluene, dimethylformamide, and the like but are generally not very soluble in water.

The novel 4-[(monosubstituted-alkyl)amino]benzoic acids and analogs of the present invention which are organic bases may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hyrobromic, trifluoroacetic, citric, tartaric, ascorbic, and the like. The novel compounds of the present invention in their acidic forms or which contain acidic substituents are converted to their organic or inorganic cationic salts for therapeutic use. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of 1-methylglucamine are prepared by dissolving equimolar amounts of the acid and the base in hot ethanol or aqueous alcohols and cooling to crystallization.

Many of the novel 4-[(monosubstituted-alkyl)amino]-benzoic acids, esters, and amides of the present invention are prepared by reactions of the corresponding 4-aminobenzoic acid, ester, or amide with an appropriate alkylating or acylating agent followed by chemical modification of the monosubstituted-alkyl group. Alkylating and acylating agents especially suitable for these reactions are hydroxyalkyl halides and haloalkanoic acids, which are generally known in the chemical literature. Those which are not known are readily prepared from the corresponding hydroxyalkanoic acids either by reduction of the carboxylic acid group with reagents such as the alkali metal hydrides or by replacement of the hydroxy group with halogen with reagents such as hydrogen bromide. In certain cases, chemical modification of the monosubstituted-alkyl moiety before, rather than after the alkylation or acylation reaction as described above, is preferable. In these cases, reactions similar to those described subsequently for the interchange of substituents in 4-[(monosubstituted-alkyl)amino]phenyl compounds are employed.

Alkylation of the appropriate 4-aminophenyl compounds with suitable alkylating agents such as halides, sulfates, tosylates or trifluoromethanesulfonates is carried out with or without solvent at 50° C.-150° C. Suitable solvents are lower alkanols, chloroform, N,N-dimethylformamide, N,N-dimethylacetamide, diglyme, dimethylsulfoxide, acetonitrile, toluene, benzene, hexamethylphosphoramide and the like. The reaction may be carried out with an equivalent of base such as an alkali carbonate or bicarbonate, or with a catalytic amount of copper powder when substituted alkyl halides are used as the alkylating agent. Alternatively, alkylation of the sodium salt (formed with sodium hydride) of either the amino group of a 4-aminophenyl compound or the anilide moiety of a 4-(acetylamino)phenyl compound yields the desired alkylation product or an N-acetyl derivative thereof. Other 4-aminophenyl compounds useful in these alkylation reactions, or in the subsequently described acylation reactions, are for example, 4-aminobenzonitrile, p-toluidine, and the acetal of 4-aminobenzaldehyde. In these cases, the desired alkylation product is obtained by a subsequent oxidative or hydrolytic transformation of the nitrile, methyl, or acetal group.

Acylation of a 4-aminophenyl compound followed by diborane reduction of the resulting 4-(acylamino)phenyl compounds at room temperature or above for 1–16 hours also yields certain of the 4-[(monosubstituted-alkyl)amino]phenyl compounds of the present invention. An alternative method for the reduction of 4-(acylamino)benzoate esters or 4-(acylamino)benzamides involves reaction of these intermediates with phosphorus oxychloride followed by reduction of the resulting chloroimides with sodium borohydride.

An alternative method for the preparation of certain of the desired alkylation products involves reductive alkylation of a 4-aminobenzoic ester or amide with a substituted aldehyde or ketone. The 4-aminobenzoic ester or amide itself may be used or it may be generated in situ by reduction of a 4-amino group precursor such as the 4-nitro group.

Two types of substitution reactions also yield certain of the 4-[(monosubstituted-alkyl)amino]phenyl compounds of the present invention. The reaction of esters of 3,4-didehydrobenzoic acid with an alkylamine (or its alkali metal salt), or Friedel-Crafts acylation of an N-alkylanilic or N-acyl-N-alkylaniline yields certain of the desired compounds or intermediates thereto. The former type of reaction, in which the 3,4-didehydrobenzoic acid is generated in situ is carried out by treating a 4-halobenzoate ester or disubstrituted amide such as phenyl 4-bromobenzoate with the lithium, potassium or sodium salt of excess alkylamine such as 11-(n-butylthio)undecylamine in diethyl ether or other aprotic solvent. The second method comprises reacting N-(11-methylthiohexadecyl)aniline and the like or its N-acetyl derivative with a carboalkoxy chloride or oxalyl chloride and anhydrous aluminum chloride in dry diethyl ether, halocarbon or hydrocarbon medium.

The 4-[(monosubstituted-alkyl)amino]benzoic acids of the present invention may be obtained by hydrolysis of the corresponding 4-[(monosubstituted-alkyl)amino]benzoate esters in boiling aqueous ethanolic alkali followed by acidification. Alternatively, these benzoic acids may be isolated as their alkali metal salts.

The novel 4-[(monosubstituted-alkyl)amino]benzoic esters and amides of the present invention may be readily prepared by treating the corresponding acid halides, mixed acid anhydrides, or activated estrs or amides with an appropriate hydroxy compound, amine, or salt of a carboxamide or sulfonamide. These reactions are preferably carried out in an inert solvent at a temperature of 25°–125° C. for a period of time from about 30 minutes to 18 hours or more. In the case of the acid halide and other acid-forming acylating agents, the reaction is carried out in the presence of an acid scavenger such as diisopropylethylamine, 4-dimethylaminopyridine, pyridine, triethylamine, finely powdeed sodium carbonate, and the like. The acid halide and anhydride starting materials may be obtained from the corresponding 4-(monosubstituted-monoalkylamino)benzoic acids by methods which are well-known in the art or described herein. However, a protecting group on the arylamino nitrogen is used for best results. The simplest protecting group is provided by protonation of the amine to give an anilinium salt prior to or during formation of the acylating agent. Acylation of this amino group by carefully selected acyl groups such as carbobenzyloxy, carbo-t-butoxy, and trifluoroacetyl provides protecting of this group from self-acylation during ester or amide formation. These protecting groups are then removed by catalytic hydrogenation, mild acid treatment, and mild alkali treatment, respectively. Activated esters or amides, which are used to synthesize the esters or amides of the present invention, are carboxymethyl, 4-nitrophenyl, N-oxysuccinimide, 1-imidazolyl and the like. In certain cases, treatment of acids or ordinary esters such as methyl or ethyl with an excess of an appropriate hydroxy-containing substrate in the presence of a Lewis or mineral acid such as boron trifluoride, sulfuric acid, or hydrochloric acid is sufficient to convert the 4-(monosubstituted-monoalkylamino)benzoic esters or acids to the appropriate esters.

With certain kinds of substrates for ester formation, it is necessary to form the alkali metal or strong organic base salts of the 4-[(monosubstituted-alkyl)amino]benzoic acids in order to react them with the various halo-, methanesulfonate- or p-toluenesulfonate-containing substrates. Certain 4-[(monosubstituted-alkyl)amino]benzoate esters may be prepared by the reaction of 4-[(monosubstituted-alkyl)amino]benzoic acids with diazoalkyl compounds such as ethyl diazoacetate and the like, obtained by reaction of nitrous acid or alkyl nitrite on α- or β-aminoalkanoate esters.

The (monosubstituted-alkylamino)benzoate esters or amides are also prepared by de-acylation of the corresponding 4-(N-trifluoroacetyl-monosubstituted-alkylamino)benzoate esters or amides by reaction with an alkali hydroxide such as sodium or potassium in a lower alkanol, water or an aqueous lower alkanol at 5° C. to 50° C. Alternatively, the 4-[(monosubstituted-alkyl)amino]benzoate esters or amides may be prepared by de-acylation of the 4-(N-carbo-t-butoxy-N-alkylamino)benzoate esters or amides with mineral acids such as hydrochloric or hydrobromic acid, preferably in glacial acetic acid or with anhydrous trifluoroacetic acid at 0° C. to 50° C. Also these compounds are prepared by removal of the carbobenzyloxy protecting group from the anilino nitrogen atom by means of catalytic hydrogenation or treatment with a mineral acid such as hydrobromic acid, preferably in glacial acetic acid.

With certain kinds of substrates for amide formation, it is necessary to form the alkali metal or strong organic base salts of these substrates in order to react them with the various aforementioned acylating forms of the 4-[(monosubstituted-alkyl)amino]benzoic acids. The aminoalkanecarboxylic and aminoalkanesulfonic acids are zwitterionic and must be converted to their salts, suitably in situ. They may also be used in the form of their esters and then hydrolyzed after amide formation. Certain substrates, which are neutral like the carboxamides or slightly acidic like the alkane or arenesulfonamides, are converted to reactive sodium salts by reaction with sodium hydride or other basic reagents.

Certain N-substituted derivatives of the amino nitrogen atoms are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)alkyl derivatives are obtained by reaction of the 4-[(monosubstituted-alkyl)amino]benzoic acid, ester or amide with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediates as well as to the carbon-carbon double bond of cinnamaldehyde itself.

In certain cases, unsaturation is introduced at a late stage of the preparation of 4-(monosubstituted-unsaturated alkylamino)benzoic acid derivatives. For example, an alkyl 4-(monosubstituted-ω-haloalkylamino)benzoate is dehydrohalogenated to the corresponding olefinic compound or, alternatively, it is converted to a Wittig trialkylphosphonium reagent and reacted with an aldehyde to yield a product with an internal double bond. This ω-halo substrate is also reacted with an alkylacetylene sodium or lithium salt to form 4-(monosubstituted-alkynylamino)benzoic acid derivatives. In other cases, a 4-(monosubstituted-unsaturated alkylamino)benzoic acid derivative is converted to the corresponding saturated derivative by catalytic hydrogenation. In still other cases, a 4-(unsubstituted-unsaturated alkylamino)benzoic acid derivative is converted to the desired 4-(monosubstituted-monoalkylamino)benzoic acid derivative by the addition of a reagent to the double or triple bond. An example of this type of reaction is the addition of hydrogen bromide to ethyl 4-(11-undecenylamino)benzoate to yield ethyl 4-(10-bromoundecylamino)benzoate.

Many of the novel compounds of the present invention are prepared by chemical modifications of the substituent already present in a 4-[(monosubstituted-alkyl)amino]phenyl compound. An example of this type of modification is the conversion of a hydroxy substituent to a group activated for displacement, such as a methanesulfonate or p-toluenesulfonate ester. This modification is accomplished by methods well known to those skilled in the art. Alternatively, the hydroxy substituent may be converted to a halogen substituent, for example, the reaction of 4-(11-hydroxyundecylamino)benzoic acid with hydrogen bromide affords 4-(11-bromoundecylamino)benzoic acid.

Displacement reactions of the above described sulfonate esters and halides may be carried out with a variety of nucleophiles, such as, for example, thiourea, potassium thioacetate, sodium thiophenoxide, the sodium or potassium salt of 2-mercaptopropane or 3-(p-chlorophenyl)propanethiol, the sodium salt of methanesulfonamide, sodium azide, potassium chloride, sodium iodide and the like. These displacement reactions yield 4-(monosubstituted-monoalkylamino)phenyl compounds, monosubstitutents such as, thiuronium halide, acetylthio, phenylthio, 2-propylthio, 3-(p-chlorophenyl)-propylthio, amino, anilino, azido, chloro, iodo, and the like. Hydrolysis of the thioacetates or thiuronium salts resulting from these displacements affords mercapto substituted 4-(monoalkylamino)phenyl compounds. The mercapto 4-(monoalkylamino)phenyl compounds may be alkylated with alkyl or aralkyl halides to yield alkylthio- or aralkylthio-substituted 4-(monoalkylamino)phenyl compounds. Oxidation of these alkylthio- or aralkylthio-substituted derivatives or the previously mentioned arylthio-substituted 4-(monoalkylamino)phenyl compounds with one equivalent of an oxidizing agent such as m-chloroperbenzoic acid affords the corresponding sulfoxides. Oxidation of these derivatives with excess oxidizing agent yields the corresponding sulfones. These sulfinyl and sulfonyl alkyl derivatives are also obtained by alkylation of aminophenyl compounds such as ethyl 4-aminobenzoate with sulfinyl or sulfonyl-substituted alkyl halides or sulfonates.

The alkylation of certain 4-aminophenyl compounds with haloketones yields 4-(alkanoylalkylamino)phenyl compounds, for example, alkylation of ethyl 4-aminobenzoate with 1-bromo-6-hexadecanone (obtained by the reaction of 6-bromohexanoyl chloride with n-decyl magnesium bromide in the presence of cadmium chloride) yields ethyl 4-(6-oxohexadecylamino)benzoate. Carbonyl derivatives of this type may be reduced to the corresponding alcohols with diborane, converted to tertiary alcohols by reaction with Grignard or alkyllithium reagents, or converted to the corresponding oximes by reaction with hydroxylamine hydrochloride.

The novel compounds of the present invention are not only potent hypolipidemic agents but also prevent or diminish the formulation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypochlolesteremic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjuction with the following specific examples.

EXAMPLE 1

Preparation of 16-bromohexadecanoic acid

A mixture of 18 g. of 16-hydroxyhexadecanoic acid and 160 g. of 30–32% hydrogen bromide in acetic acid is treated with 32 ml. of concentrated sulfuric acid and stirred at ambient temperature for 18 hours. The solution is stirred under reflux for 7 hours and then poured into 500 ml. of ice-water and filtered. A methylene chloride solution of the product is Darco clarified, dried over magnesium sulfate, and evaporated. Crystallization of the residue from ether-petroleum ether and then acetonitrile affords 16-bromohexadecanoic acid as a white solid.

EXAMPLE 2

Preparation of 11-bromoundecanol

A solution of 5 g. of 11-bromoundecanoic acid and 20 ml. of tetrahydrofuran is stirred at 0° C. while 16 ml. of 1 M borane in tetrahydrofuran is added during 15 minutes. The mixture is stirred 18 hours at ambient temperature, poured into ice-water, and extracted with ether. The dried extract is evaporated and the residual oil crystallized from hexane to yield 11-bromoundecanol as a white solid.

EXAMPLE 3

Preparation of 1-methanesulfonyloxy-10-undecene

To a solution of 10-undecen-1-ol (15.0 g.) and triethylamine (14 ml.) in dry methylene chloride (320 ml.) at −8° C. is added methanesulfonylchloride (5.73 ml.), dropwise. The reaction mixture is stirred at −10° C. for 30 minutes and then diluted with methylene chloride, extracted with ice-water (250 ml.), followed by cold 10% hydrochloric acid (200 ml.); cold saturated sodium bicarbonate (200 ml.) and cold brine (200 ml.). The organic phase is dried over magnesium sulfate and the solvent removed in vacuo to provide the mesylate as an oil.

EXAMPLE 4

Preparation of 6-oxohexadecyl bromide

The Grignard reagent prepared from 60 g. of decyl bromide, 5.6 g. of magnesium, and 200 ml. of ether is treated with 27 g. of cadmium chloride and the solution is stirred under reflux for 30 minutes. The solvent is replaced by distillation with toluene, and the toluene solution is treated with 29 g. of 6-bromohexanoyl chloride and stirred under reflux for 30 minutes. The mixture is cooled, diluted with 200 ml. of 10% sulfuric acid, and extracted with ether. The extracts are dried and evaporated and the residual oil distilled in vacuo to yield 6-oxohexadecyl bromide as a light yellow oil.

EXAMPLE 5

Preparation of ethyl 4-(11-hydroxyundecylamino)benzoate

A solution of 16 g. of 11-bromoundecanol, 9.9 g. of ethyl 4-aminobenzoate, and 6.0 g. of triethylamine in 50 ml. of hexamethylphosphoramide is stirred at 70° C. under argon for 128 hours. The resulting solution is cooled, diluted with water, and filtered. Recrystallization of the solid from acetonitrile affords ethyl 4-(11-hydroxyundecylamino)benzoate as a white, crystalline solid.

EXAMPLE 6

Preparation of ethyl 4-(10-undecenylamino)benzoate

A solution of 14.0 g. of 1-methanesulfonyloxy-10-undecene and 19.8 g. of ethyl p-aminobenzoate in hexamethylphosphoramide is heated at 120° C. for 20 hours. After cooling the reaction mixture is diluted with ethanol:water (1:1) (30 ml.) and chilled. More ethanol is added and the solid material is collected. This solid is recrystallized from ethanol to yield ethyl 4-(10-undecenylamino)benzoate as a white solid.

EXAMPLE 7

Preparation of ethyl 4-(6-oxohexadecylamino)benzoate

A solution of 15 g. of 6-oxohexadecyl bromide and 15.6 g. of ethyl 4-aminobenzoate in 60 ml. of hexamethylphosphoramide is stirred at 120° C. for 18 hours, allowed to cool, and diluted with water. The mixture is filtered and the resulting solid is dissolved in methylene chloride. The solution is washed with diluted hydrochloric acid, dried, and evaporated to yield a brown solid. Crystallization from ethanol yields ethyl 4-(6-oxohexadecylamino)benzoate as a white solid.

EXAMPLE 8

Preparation of 4-(16-hydroxyhexadecylamino)benzonitrile p-Aminobenzonitrile (12 g.) and 16-bromo-1-hexadecanol (15 g.) are dissolved in hexamethylphosphoramide (200 ml.) and heated under nitrogen in an oil bath maintained at 120° C. for 22 hours. The reaction mixture is cooled to room temperature and water (50 ml.) is added gradually. The mixture is then chilled in an ice-bath. The precipitate separated is filtered, washed thoroughly with water, and dried. It is then washed repeatedly with hexane and dried. The pale brownish yellow granular solid is obtained as a homogeneous product. Recrystallization from ether-hexane affords 4-(16-hydroxyhexadecylamino)benzonitrile as pale yellow prisms.

EXAMPLE 9

Preparation of 1-[4-(14-hydroxytetradecylamino)benzoyl]pyrrolidine

A solution of 10 g. of 14-hydroxytetradecyl bromide and 10.8 g. of ethyl 1-(4-aminobenzoyl)pyrrolidine in 75 ml. hexamethylphosphoramide is heated at 110° C. for 17 hours. The cooled solution is diluted with 100 ml. water, filtered, and the residue is washed in portions with 100 ml. 50% ethanol-water. After drying the product is crystallized from ethanol to yield 1-[4-(14-hydroxytetradecylamino)benzoyl]pyrrolidine as a white solid.

EXAMPLE 10

Preparation of 4-(11-hydroxyundecylamino)benzoic acid

A solution of 5 g. of ethyl 4-(11-hydroxyundecylamino)benzoate in 75 ml. 95% ethanol is saponified with 2.5 g. of 85% potassium hydroxide by refluxing for 5 hours. The warm solution is diluted with 150 ml. water and adjusted to pH 5 with 37% hydrochloric acid. The precipitate is filtered, washed with water, dried in vacuo and crystallized from acetic acid to yield 4-(11-hydroxyundecylamino)benzoic acid as a white solid.

EXAMPLE 11

Preparation of 4-(16-bromohexadecylamino)benzaldehyde

Di-iso-butylaluminum hydride (54 ml., 25% solution in toluene) is added with stirring to a solution of 4-(16-bromohexadecylamino)benzonitrile (11.4 g.) under a nitrogen atmosphere. The temperature rises to 40° C. during the 30 minute addition and then the reaction is then stirred for 1 hour. A solution of methanol in toluene (50 ml., 1:1) was added over 30 minutes and the mixture is poured into vigorously stirred ice-cold aqueous sulfuric acid (50 ml., 5%). After 10 minutes diatomaceous earth (30 g.) is added, the mixture filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. The crude product is recrystallized from dichloromethane-hexane to yield 4-(16-bromohexadecylamino)benzaldehyde as a white solid.

EXAMPLE 12

Preparation of ethyl 4-(11-bromoundecanamido)benzoate

A solution of 20 g. of 11-bromoundecanoyl chloride in 100 ml. of methylene chloride is slowly added with stirring to a solution of 20 g. of ethyl 4-aminobenzoate in 100 ml. of methylene chloride. The mixture is filtered and the filtrate is washed with dilute hydrochloric acid and water, dried, and evaporated. Crystallization from acetonitrile affords ethyl 4-(11-bromoundecanamido)benzoate as a white solid.

EXAMPLE 13

Preparation of ethyl 4-(11-bromoundecylamino)benzoate

A solution of 5 g. of ethyl 4-(11-bromoundecanamido)benzoate in 50 ml. of tetrahydrofuran is slowly added with stirring to 13 ml. of 1 M borane in tetrahydrofuran. The solution is poured into 50 ml. of dilute hydrochloric acid and the resulting mixture is filtered. The solid is crystallized from acetonitrile to yield ethyl 4-(11-bromoundecylamino)benzoate as a white, crystalline solid.

EXAMPLE 14

Preparation of ethyl 4-(3-benzylthiopropylamino)benzoate

A mixture of 17 g. of ethyl 4-aminobenzoate and 14 g. of 3-benzylthiopropionaldehyde in 100 ml. of absolute ethanol is heated on a steam bath for 10 minutes. The solid which separates upon cooling the mixture is collected, dried, and redissolved in 200 ml. of hot ethanol. The solution is treated portion-wise with 4 g. of sodium borohydride and the stirred mixture is refluxed for 3 hours. Dilution with water and filtration yields ethyl 4-(3-benzylthiopropylamino)benzoate as a white, crystalline solid.

EXAMPLE 15

Preparation of sodium 4-(11-hydroxyundecylamino)benzoate

A mixture of 3.62 g. of 4-(11-hydroxyundecylamino)benzoic acid and 25 ml. of ethanol-water (9:1) containing 400 mg. of sodium hydroxide is stirred for 4 hours. The mixture is filtered and the solid washed with ethanol-water and dried in vacuo to yield sodium 4-(11-hydroxyundecylamino)benzoate as a white, amorphous solid.

TABLE I

Acyl halides required for the preparation of compounds shown in the table are obtained from the corresponding carboxylic acids, some of which are prepared by the method of Example 1, by treatment with thionyl chloride. Many of the alkyl halides and sulfonate esters required for the preparation of these compounds are prepared by the methods of Examples 2-4. The 4-aminophenyl compounds shown in the table are prepared by reactions of these materials with appropriate 4-aminophenyl derivatives by the methods of Examples 5-15 as shown in the table.

TABLE I

| Example No. | Methods of Examples | Product |
|---|---|---|
| 16 | 5, 10 | 4-(16-Hydroxyhexadecylamino)benzoic acid |
| 17 | 5, 10 | 4-(14-Hydroxytetradecylamino)benzoic acid |
| 18 | 5, 10 | 4-(8-Hydroxyoctylamino)benzoic acid |
| 19 | 5, 10 | 4-[5-Hydroxy-1-(n-butyl)pentylamino]benzoic aicd |
| 20 | 5, 10 | 4-(11-Hydroxyundec-2-enylamino)benzoic acid |
| 21 | 5, 10 | 4-(16-Hydroxyhexadec-7-enylamino)benzoic acid |
| 22 | 5, 10 | 4-[11-Hydroxy-1-(n-pentyl)undec-2-ynylamino]benzoic acid |
| 23 | 5, 10 | 4-[(3-Hydroxy-2,6,6-trimethylcyclohexyl)methylamino]benzoic acid |
| 24 | 6 | Ethyl 4-(4-pentadecenylamino)benzoate |
| 25 | 6 | Ethyl 4-(2-hexadecenylamino)benzoate |
| 26 | 6 | Ethyl 4-(9-octadecenylamino)benzoate |
| 27 | 6 | Ethyl 4-(15-hexadecenylamino)benzoate |
| 28 | 7, 10 | 4-(11-Oxohexadecylamino)benzoic acid |
| 29 | 7, 10 | 4-(6-Oxotetradecylamino)benzoic acid |
| 30 | 7, 10 | 4-(3-Oxoundecylamino)benzoic acid |
| 31 | 8, 11 | 4-(14-Chlorotetradecylamino)benzaldehyde |
| 32 | 8, 11 | 4-[11-(n-Butylthio)undecylamino]benzaldehyde |
| 33 | 8, 11 | 4-(2-Benzylthioundecylamino)benzaldehyde |
| 34 | 9 | 1-[4-(11-Benzylthioundecylamino)benzoyl]pyrrolidine |
| 35 | 9 | 1-[4-(6-Oxoundecylamino)benzoyl]piperidine |
| 36 | 9 | 1-[4-(16-Hydroxyhexadecylamino)benzoyl]pyrrolidine |
| 37 | 12, 13, 10 | 4-(16-Bromohexadecylamino)benzoic acid |
| 38 | 12, 13, 10 | 4-[(3-Bromo-2,2,4-trimethylcyclopentyl)methylamino]benzoic acid |
| 39 | 12, 13, 10 | 4-(2-Benzylthiooctylamino)benzoic acid |
| 40 | 12, 13, 10 | 4-(11-methylthioundecylamino)benzoic acid |
| 41 | 12, 13, 10 | 4-(18-Bromooctadecylamino)benzoic acid |
| 42 | 12, 13, 10 | 4-[8-Bromo-2-(n-butyl)octylamino]benzoic aicd |
| 43 | 12, 13, 10 | 4-(12-Bromooctadecylamino)benzoic acid |
| 44 | 14, 10 | 4-[4-(4-Chlorophenylthio)octylamino]benzoic acid |
| 45 | 14, 10 | 4-(2-Methylthiotetradecylamino)benzoic acid |
| 46 | 14, 10 | 4-(11-Phenylthioundec-2-enylamino)benzoic acid |
| 47 | 15 | Sodium 4-(16-bromohexadecylamino)benzoate |
| 48 | 15 | Sodium 4-(16-hydroxyhexadecylamino)benzoate |
| 49 | 15 | Sodium 4-(11-methylthioundecylamino)benzoate |
| 50 | 5, 10 | 4-(3-Hydroxytetradecylamino)benzoic acid |
| 51 | 6 | Ethyl 4-(9-hexadecenylamino)benzoate |
| 52 | 7, 10 | 4-(3-Oxotetradecylamino)benzoic acid |
| 53 | 8, 11 | 4-(16-Methylthiohexadecylamino)benzaldehyde |
| 54 | 9 | 1-[4-(11-Benylthioundecylamino)benzoyl]morpholine |

EXAMPLE 55

Preparation of 4-(16-bromohexadecylamino)benzoyl chloride hydrochloride

A cold solution of 25 g. 4-(16-bromohexadecylamino)benzoic acid in 500 ml. dimethoxyethane-methylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield an orange, semi-crystalline mass.

EXAMPLE 56

Preparation of N-trifluoroacetyl-4-(16-bromohexadecylamino)benzoyl chloride

To a stirred, ice-cold suspension of 9 g. 4-(16-bromohexadecylamino)benzoic acid in 100 ml. dimethoxyethane and 16 ml. pyridine is treated with 18 ml. trifluoroacetic anhydride. The solution is stirred at 0° C. for 30 minutes at room temperature. The solution is diluted with 300 ml. ether and 100 g. ice. After stirring vigorously for 15 minutes, the phases are separated, the ether solution is washed with brine, dried and evaporated to a white, amorphous solid.

To 9.2 g. of the above product in 30 ml. methylene chloride and 0.5 ml. dimethylformamide is added 5.7 ml. thionyl chloride. After 20 hours at reflux, the solvents are evaporated to yield a light yellow, mobile oil.

EXAMPLE 57

N-Carbobenzyloxy-4-(16-bromohexadecylamino)benzoyl chloride

To 15 g. 4-(16-bromohexadecylamino)benzoic acid in 200 ml. warm chloroform is added 15 g. sodium carbonate in 150 ml. water. To the vigorously solution is added 10 g. carbobenzyloxy chloride. After 2 hours stirring at 40° C., the layers are separated, washed three times with 1 N hydrochloric acid dried, and evaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time to yield a viscous, orange oil.

EXAMPLE 58

Preparation of
1-{4-[N-(t-butyloxycarbonyl)-N-(16-bromohexadecyl)amino]benzoyl}imidazole To a solution of 10 g. 4-(16-bromohexadecylamino)benzoic acid in 100 ml. of dioxane is treated with 4.0 g. t-butylazidoformate and 10 ml. pyridine. After stirring at room temperature for 18 hours, protected amido-acid is precipitated from solution by addition of 150 ml. water. The product is collected and thoroughly dried. The crude product is dissolved in 200 ml. of a mixture consisting of methylene chloride/dimethoxyethane/pyridine (1:4:1), and to this is added 5.4 g. 1,1'-carbonyldiimidazole. The solution is stirred overnight at room temperature and the solvents are evaporated to yield the title compound as a thick, orange oil.

EXAMPLE 59

Preparation of potassium sulfomethyl 4-(11-hydroxyundecylamino)benzoate

To 39.3 g. of potassium 4-(11-hydroxyundecylamino)benzoate in 125 ml. of hexamethylphosphoramide is added 26.0 g. of powdered potassium iodomethanesulfonate. After stirring for 24 hours at 25° C., the product is obtained by careful dilution with water or alcohol to the crystallization point.

When this reaction is carried out with potassium 2-iodoethansulfonate, the potassium sulfoethyl ester is obtained.

EXAMPLE 60

2,3-Dihydroxypropyl 4-(11-hydroxyundecylamino)benzoate

A solution of 7.34 g. of 4-(11-hydroxyundecylamino)benzoic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield 2,3-dihydroxypropyl 4-(11-hydroxyundecylamino)benzoate.

EXAMPLE 61

2,3-Dihydroxypropyl 4-(16-bromohexadecylamino)benzoate

A solution of 11.8 g. of 4-(16-bromohexadecylamino)benzoic acid, 1.00 g. of glycerol, and 5.35 ml. of boron trifluoride etherate in 200 ml. of toluene is stirred under reflux for 48 hours. The solution is treated with an additional 5.35 ml. of boron trifluoride etherate and refluxing for 120 hours. Dilution with water and methylene chloride followed by filtration affords 2,3-dihydroxypropyl 4-(16-bromohexadecylamino)benzoate as a white solid.

EXAMPLE 62

2,3-Dihydroxypropyl 4-(11-bromoundecylamino)benzoate

A mixture of 2.25 g. of methyl 4-(11-bromoundecylamino)benzoate, 280 mg. of glycerol, and 1.37 g. of p-toluenesulfonic acid is heated at 180° C. for 18 hours and then is partitioned between ether and 3% aqueous sodium carbonate solution. The ether layer is separated, dried, and evaporated to yield 2,3-dihydroxypropyl 4-(11-bromoundecylamino)benzoate.

EXAMPLE 63

Methyl 4-(16-bromohexadecylamino)benzoate

A solution of 50.5 g. of 4-(16-bromohexadecylamino)benzoic acid and 34.4 ml. of boron trifluoride etherate in 200 ml. of methanol is stirred under reflux for 44 hours, allowed to cool, and is poured into 1.20 liters of ice-cold 5% aqueous sodium carbonate solution. The white solid is collected by filtration and recrystallized from benzene-ethanol to yield methyl 4-(16-bromohexadecylamino)benzoate, m.p. 92°–93° C.

EXAMPLE 64

Preparation of 1-(methoxycarbonyl)propyl 4-(16-bromohexadecylamino)benzoate

To a solution of 10.0 g. 4-(16-bromohexadecylamino)benzoyl chloride hydrochloride in 200 ml. methylene chloride is added dropwise a solution of 3 g. methyl α-hydroxy butyrate and 5 g. triethylamine in 100 ml. ether. After 17 hours stirring at room temperature, the precipitate is filtered and washed with several portions of ether. The ether solution is washed with water, dried, and condensed to the crystalline title compound.

EXAMPLE 65

Preparation of 1-carboxyethyl 4-(16-bromohexadecylamino)benzoate

A flask containing 10.0 g. 4-(16-bromohexadecylamino)benzoic acid, 3.3 g. lactic acid, 500 mg. toluenesulfonic acid and 500 ml. toluene is equipped with a Soxhlet extractor charged with activated 4 Å Linde molecular sieves. The solution is refluxed for 24 hours, during which time the Soxhlet extractor is charged twice more with fresh sieves. The hot solution is filtered and left to cool, whereupon the product separates as off-white crystals.

EXAMPLE 66

Preparation of diethyl O-[4-(16-bromohexadecylamino)benzoyl]tartarate

N-Trifluoroacetyl-4-(16-bromohexadecylamino)benzoyl chloride and 1.2 g. triethylamine in 100 ml. warm ether is treated with 2.5 g. diethyl tartarate and refluxed for 24 hours. The hot solution is filtered, the residue is washed with hot ether, and the solution is evaporated. After treatment with aqueous methanolic potassium carbonate, the product is precipitated by acidification, filtered and dried. Crystallization from acetone yields the diethyl tartarate as a white, crystalline solid.

EXAMPLE 67

Preparation of O-[4-(16-bromohexadecylamino)benzoyl]malic acid

To a warm solution of N-carbobenzyloxy-4-(16-bromohexadecylamino)benzoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, the solution is evaporated, and the residue is crystallized from acetic acid to yield the title compound as a tan, crystalline mass.

EXAMPLE 68

Preparation of 2-(ethoxycarbonyl)vinyl 4-(16-bromohexadecylamino)benzoate

To a mixture containing 4.3 g. 1-{4-[N-(t-butyloxycarbonyl)-N-(16-bromohexadecyl)amino]benzoyl}-imidazole, 50 ml. chloroform, in 50 ml. 5 N sodium hydroxide is added 3 g. ethyl α-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 4-(16-bromohexadecylamino)benzoate.

EXAMPLE 69

Preparation of 2-(ethoxycarbonyl)ethyl 4-(16-bromohexadecylamino)benzoate

A solution of 4 g. 2-(ethoxycarbonyl)vinyl 4-(16-bromohexadecylamino)benzoate and 400 mg. 10% palladium-on-carbon in 100 ml. tetrahydrofuran is hydrogenated at 50 psi until hydrogen uptake stops. The catalyst is filtered, the solution is evaporated, and the residue is crystallized from acetonitrile to yield 2-(ethoxycarbonyl)ethyl 4-(16-bromohexadecylamino)benzoate.

TABLE II

The benzoic acid derivatives required for the preparation of the benzoate esters of the table are prepared from the corresponding acids by the methods of Examples 55–58. The carboxylic acids required are prepared by the methods of Examples 5–15 or 149–162. The benzoate esters of the table are prepared from these carboxylic acids or derivatives thereof by the methods of Examples 59–69.

| Ex. No. | Method of Example | Product |
|---|---|---|
| 70 | 59 | Potassium sulfomethyl 4-(2-hydroxytetradecylamino)benzoate |
| 71 | 59 | Ethyl 0-[4-(11-hydroxyundec-2-enyl-amino)benzoyl]glycolate |
| 72 | 60 | 2,3-Dihydroxypropyl 4-[11-hydroxy-1-(n-pentyl)undec-2-ynylamino]benzoate |
| 73 | 60 | 2,3-Dihydroxypropyl 4-(6-oxotetradecylamino)benzoate |
| 74 | 60 | 2,3-Dihydroxypropyl 4-(11-benzylthioundecylamino)benzoate |
| 75 | 60 | 3-Hydroxypropyl 4-(11-methylsulfonylundecylamino)benzoate |
| 76 | 60 | 2-Hydroxypropyl 4-(16-azidohexadecylamino)benzoate |
| 77 | 59 | 2-{4-[(11-benzylsulfinyl)undecylamino]benzoyl}ethanesulfonic acid |
| 78 | 59 | Potassium sulfomethyl 4-[(3-acetamido-2,6,6-trimethylcyclohexyl)methylamino]benzoate |
| 79 | 61 | 2-Ethoxyethyl 4-(11-oxohexadecylamino)benzoate |
| 80 | 61 | Isopropyl 4-[11-(n-butylsulfonyl)undecylamino]benzoate |
| 81 | 61 | 2-Dimethylaminoethyl 4-(3-oxoundecylamino)benzoate |
| 82 | 61 | 2-Ethoxyethyl 4-(2-methylsulfinyltetradecylamino)benzoate |
| 83 | 63 | Methyl 4-(16-chlorohexadecylamino)benzoate |

-continued

| Ex. No. | Method of Example | Product |
|---|---|---|
| 84 | 63 | Methyl 4-(2-benzylsulfonyloctylamino)benzoate |
| 85 | 63 | Methyl 4-(2-benzamidooctylamino)benzoate |
| 86 | 63 | Methyl 4-(11-phenylaminoundecylamino)benzoate |
| 87 | 62 | 3-Hydroxypropyl 4-(16-iodohexadecylamino)benzoate |
| 88 | 62 | 4-Hydroxybutyl 4-(2-azidotetradecylamino)benzoate |
| 89 | 64 | 4-Fluorophenyl 4-[11-(n-butylsulfonyl)undecylamino]benzoate |
| 90 | 64 | 3-Methylbenzyl 4-[(8-benzylsulfinyl)octylamino]benzoate |
| 91 | 64 | 4-Pyridylmethyl 4-(2-chlorotetradecylamino)benzoate |
| 92 | 64 | 2,6-Dichlorophenyl 4-(10-methylthiodec-2-enylamino)benzoate |
| 93 | 64 | 1-Methyl-4-piperidyl 4-(16-chlorohexadecylamino)benzoate |
| 94 | 64 | Allyl 4-(6-oxoundecylamino)benzoate |
| 95 | 64 | 2,3-Epoxypropyl 4-(11-chlorohexadecylamino)benzoate |
| 96 | 65 | 1-Carboxyethyl 4-[(3-bromo-2,2,4-trimethylcyclopentyl)methylamino]benzoate |
| 97 | 65 | 1-Carboxymethyl 4-(2-methylsulfonyltetradecylamino)benzoate |
| 98 | 65 | 1-Carboxyethyl 4-[11-(4-chlorophenylsulfonyl)undec-2-enylamino]benzoate |
| 99 | 65 | Tetrahydropyranyl 4-(14-chlorotetradecylamino)benzoate |
| 100 | 65 | Tetrahydropyranyl 4-(2-oxotetradecylamino)benzoate |
| 101 | 66 | Diethyl 0-[4-(6-oxoundecylamino)benzoyl]tartarate |
| 102 | 66 | Diethyl 0-[4-(16-chlorohexadec-7-enylamino)benzoyl]tartarate |
| 103 | 66 | Diethyl 0-[4-(11-iodo-1-methylundec-2-ynylamino)benzoyl]tartarate |
| 104 | 67 | 0-[4-(8-chlorooctylamino)benzoyl]malic acid |
| 105 | 67 | 0-[4-(11-methansulfonamidoundec-2-enylamino)benzoyl]malic acid |
| 106 | 68 | 2-(Ethoxycarbonyl)vinyl 4-(10-benzylthiodecylamino)benzoate |
| 107 | 68 | 2-(Ethoxycarbonyl)vinyl 4-[(3-bromo-2,2,4-trimethylcyclopentyl)methylamino]benzoate |
| 108 | 69 | 2-(Ethoxycarbonyl)ethyl 4-(12-chlorooctadecylamino)benzoate |
| 109 | 62 | 2,3-Dihydroxypropyl 4-(14-bromotetradecylamino)benzoate |
| 110 | 62 | 2,3-Dihydroxypropyl 4-(11-chloroundecylamino)benzoate |
| 111 | 62 | 2-Hydroxypropyl 4-(11-bromoundecylamino)benzoate |

EXAMPLE 112

Preparation of 1-[4-(16-bromohexadecylamino)benzoyl]piperidine

To a chilled solution of 35 ml. of piperidine, 2.5 ml. of triethylamine and 0.6 g. of dimethylaminopyridine in 100 ml. of diethyl ether is added (½ hour) a solution of 8.3 g. of 4-(16-bromohexadecylamino)benzoyl chloride hydrochloride in 50 ml. of ether. The solution is warmed to room temperature and maintained there for two hours. The solution is heated to reflux for an additional 2 hours at which time the reaction is complete. The solution is cooled, extracted twice with 100 ml. portions of water and dried over magnesium sulfate. The solvent is removed in vacuo and the solid is recrystallized in 50 ml. of diethyl ether to yield the product.

EXAMPLE 113

Preparation of ethyl 4-(16-bromohexadecylamino)hippurate

To a solution of 18.08 g. of 4-(16-bromohexadecylamino)benzoic acid in a mixture of dioxane and methylchloride (40 ml./160 ml.) is added gaseous hydrogen chloride for 10 minutes. The slurry is cooled and 18 ml. of thionyl chloride added. The slurry is brought to reflux for 2 hours and then concentrated under vacuum (thrice diluting with dioxane each time). The final amber solution is diluted with 100 ml. of dioxane and this solution added to freshly prepared ethyl glycinate in 300 ml. of methylene chloride containing 1 g. of dimethylaminopyridine and 10 ml. of triethylamine. After 16 hours at room temperature the reaction is refluxed for 2 hours, cooled and filtered. The mother liquor is extracted with water and 10% hydrochloric acid. The solution is dried over magnesium sulfate and concentrated in vacuo to an amber liquid. A sample is preabsorbed on silica and eluted with ether giving a solid. This material is placed on a second silica column giving a second solid which is recrystallized from acetonitrile to yield the product.

EXAMPLE 114

Preparation of N-[4-(16-bromohexadecylamino)benzoyl]glycine

A mixture of 26.4 g. of ethyl N-[4-(16-bromohexadecylamino)benzoyl]glycinate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The white solid is dried in vacuo and recrystallized from acetone to yield the product.

EXAMPLE 115

Preparation of 4-(16-bromohexadecylamino)-N-(methylsulfonyl)benzamide

A solution of 19.0 g. of methanesulfonamide in 150 ml. of dry dimethyacetamide is added dropwise over 15 minutes to a stirred and cooled (water bath) suspension of 5.5 g. of sodium hydride in 100 ml. of dry dimethylacetamide. The mixture is then stirred and heated at 60°-80° 1 C. for 2 hours. In the meantime, a mixture of 36.2 g. of 4-(16-bromohexadecylamino)benzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of 4-(16-bromohexadecylamino)benzoyl chloride hydrochloride is added, in one portion, the previously prepared mixture of sodium methanesulfonamide in dimethylacetamide. The mixture becomes very hot and is cooled briefly in a water bath and then is stirred at room temperature for 30 minutes. The mixture is filtered through a bed of diatomaceous earth and the filtrate is poured into 2 l. of water. The resulting suspension is coagulated by the addition of 250 ml. of saturated sodium chloride solution and the mixture is filtered. The product is washed with water, partially air dried and then crystallized from 1.5 l. of ethanol. The product is recrystallized twice from p-dioxane and dried in the Abderhalden at 65° C. to give of the title compound as tan crystals.

EXAMPLE 116

Preparation of [4-(16-bromohexadecylamino)benzoyl]hydroxamic acid

The 16.7 g. of 4-(16-bromohexadecylamino)benzoyl chloride hydrochloride in methylene chloride is added at 5° C. to a mixture of 2.8 g. of hydroxyamine hydrochloride, 4.2 g. of sodium carbonate, and 120 ml. of ether. The mixture is stirred 3 hours after adding 10 ml. of water. After the addition of 150 ml. of water, the solvents are aerated off. The crystalline product is recrystallized from acetonitrile.

EXAMPLE 117

Preparation of 3-[4-(16-bromohexadecylamino)benzoyl]-4-carboxythiazolidine

One-tenth mole of 4-(16-bromohexadecylamino)benzoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is recrystallized from acetonitrile to yield 3-[4-(16-bromohexadecylamino)benzoyl]-4-carbethoxythiazolidine. By means of the alkaline hydrolysis method of Example 10, the ethyl ester is converted to the subject carboxylic acid. This acid is also prepared using the procedure of this Example except that the acylation of the thiazolidine-4-carboxylic acid is carried out in aqueous acetone sodium bicarbonate solution.

EXAMPLE 118

Preparation of N-[4-(16-bromohexadecylamino)benzoyl]alanine

A solution of 4.75 g. of N-trifluoroacetyl-4-(16-bromohexadecylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the product as a white, crystalline solid.

EXAMPLE 119

Preparation of 1-[4-(16-bromohexadecylamino)benzoyl]pyrrolidine

A solution of 6.0 g. of 4-[N-carbobenzyloxy-N-(16-bromohexadecyl)amino]benzoyl chloride and 1.2 g. triethylamine in 100 ml. warm ether is treated with 1.1 g. of pyrrolidine. After 1 hour at reflux, the precipitate is filtered off and washed with warm ether. After evaporation in dryness, the intermediate is dissolved in 50 ml. 30% hydrobromic/acetic acid and warmed at 50° for 2 hours. The solvents are evaporated and the product is partitioned between methylene chloride and water. The layers are separated and the methylene chloride is evaporated. The residue is crystallized from acetone to yield colorless crystals.

EXAMPLE 120

Preparation of 4-(16-bromohexadecylamino)-N-(2,3-dihydroxypropyl)benzamide

To a mixture containing 4.3 g. of 1-{4-[N-(t-butyloxycarbonyl)-N-(16-bromohexadecyl)amino]benzoyl}-imidazole, 50 ml. of chloroform, and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solid is evaporated and the residue is heated for 30 minutes at 40° C. and 50 ml. of anhydrous trifluoroacetic acid. The solvent is again evaporated and the oil is crystallized from acetone to yield the product as a light yellow crystalline solid.

TABLE III

The benzoic acid derivatives required for the preparation of the benzamides of the table are prepared from the corresponding acids by the methods of Examples 55–58. The requisite carboxylic acids are prepared by the methods of Examples 5–15 or 149–162. The benzamides of the table are prepared from these carboxylic acids or derivatives thereof by the methods of Examples 112–121.

| Example No. | Method of Example | Product |
|---|---|---|
| 121 | 112 | 1-[4-(11-Chloroundecylamino)benzoyl]morpholine |
| 122 | 112 | 1-[4-(11-Benzylsulfonylundec-2-enylamino)benzoyl]pyrrolidine |
| 123 | 112 | 1-[4-(2-Iodotetradecylamino)benzoyl]piperidine |
| 124 | 112 | N,N-Diethyl 4-[(3-methylthio-2,2,4-trimethylcyclopentyl)methylamino]benzamide |
| 125 | 113 | Ethyl 4-(13-acetamide-1-ethyltridec-2-ynylamino)hippurate |
| 126 | 113 | Ethyl 4-[(3-chloro-2,6,6-trimethylcyclohexylmethyl)amino]hippurate |
| 127 | 113 | Ethyl 4-(7-phenylsulfonyl-3-methylheptylamino)hippurate |
| 128 | 114 | N-{4-[10-Methylsulfonyl-2-(2-butenyl)-decylamino]benzoyl}glycine |
| 129 | 114 | N-[4-(8-Benzamidooctylamino)benzoyl]glycine |
| 130 | 115 | N-[4-(11-Chloroundecylamino)benzoyl]methanesulfonamide |
| 131 | 115 | N-[4-(2-Methylsulfinyltetradecylamino)benzoyl]benzamide |
| 132 | 115 | N-[4-(16-Methanesulfonamidohexadec-4-ynylamino)benzoyl]benzenesulfonamide |
| 133 | 116 | 4-[11-(p-Toluenesulfonamido)undec-2-enylamino]benzoylhydroxamic acid |
| 134 | 116 | 4-[10-(Chlorodecylamino)benzoylhydroxamic acid |
| 135 | 117 | 3-{4-[7-(p-Chlorophenylsulfonyl)3,7,7-trimethylhept-2-enylamino]benzoyl}-4-carboxythiazolidine |
| 136 | 117 | 3-{4-[10-Azido-1-(n-octyl)decylamino]-benzoyl}-4-carboxythiazolidine |
| 138 | 118 | N-[4-(16-Iodohexadecylamino)benzoyl]alanine |
| 139 | 118 | N-{4-[(16-Methylsulfinyl)hexadec-4-ynylamino]benzoyl}glycine |
| 140 | 119 | 4-(8-Phenylthio-2,7-dimethyloctylamino)benzhydrazide |
| 141 | 119 | 1-[4-(16-Methylthiohexadecylamino)-benzoyl]morpholine |
| 142 | 120 | N-[4-(11-Ethylsulfonylundec-2-enylamino)benzoyl]piperidine |
| 143 | 120 | N-[4-(16-Chlorohexadec-7-enylamino)-benzoyl]morpholine |
| 144 | 120 | 4-[8-(p-Chlorophenylsulfonyl)-2,7-dimethyloctylamino]-N-(2,3-dihydroxypropyl)benzamide |
| 145 | 120 | 4-[10-Methylsulfonyl-2-(n-hexyl)dec-4-ynylamino]-N-(2,3-dihydroxypropyl)benzamide |
| 146 | 114 | N-{4-[11-(4-Chlorobenzamide)undecylamino]benzoyl}alanine |
| 147 | 117 | 3-{4-[11-(Methylsulfonyl)undec-2-enylamino]benzoyl}-4-carboxythiazolidine |
| 148 | 118 | N-[4-(11-Chloroundec-2-enylamino)benzoyl]glycine |

EXAMPLE 149

Preparation of 4-(16-bromohexadecylamino)benzoic acid

A mixture of 16 g. of 4-(16-hydroxyhexadecylamino)benzoic acid and 150 g. of 30-32% hydrogen bromide in acetic acid is treated with 30 ml. of concentrated sulfuric acid, stirred under reflux for 8 hours, poured into ice-water, and filtered. The product is washed with water, dried and recrystallized from ether-petroleum ether to yield 4-(16-bromohexadecylamino)benzoic acid as a white, crystalline solid.

EXAMPLE 150

Preparation of Ethyl 4-(16-methanesulfonyloxyhexadecylamino)benzoate

To a solution of 14 g. of ethyl 4-(16-hydroxyhexadecylamino)benzoate and 14 ml. of triethylamine in 320 ml. of methylene chloride at −10° C. is added 6.0 ml. of methanesulfonyl chloride, dropwise. After 30 minutes at −10° C., the mixture is diluted with methylene chloride, extracted with ice-water and cold dilute hydrochloric acid, and dried over magnesium sulfate. Evaporation of the solution affords the methanesulfonate ester as an oil.

EXAMPLE 151

Preparation of 4-(11-Mercaptoundecylamino)benzoic acid

A solution of 10 g. of ethyl 4-[(11-bromoundecyl)amino]benzoate and 2.0 g. of thiourea in 80% of 95% ethanol is stirred under reflux for 3 hours, allowed to cool, treated with 12 ml. of 10 N aqueous sodium hydroxide solution and again stirred under reflux for 2 hours. The mixture is acidified with dilute hydrochloric acid and filtered. The solid is recrystallized from ethanol-water to yield the product as a white solid.

EXAMPLE 152

Preparation of Ethyl 4-(6-acetylthiohexadecylamino)benzoate

A mixture of 7.6 g. ethyl 4-(6-methanesulfonyloxyhexadecylamino)benzoate and 5.5 g. of potassium thioacetate in 200 ml. of acetone is stirred under reflux for 3 hours and evaporated. The residue is partitioned between methylene chloride and water and the organic layer is separated, dried and evaporated. Recrystallization of the residual solid from hexane affords the product as a light, tan solid. Hydrolysis of the product by the method of Example 10 affords 4-(6-mercaptohexadecylamino)benzoic acid.

EXAMPLE 153

Preparation of Ethyl 4-(11-benzylthioundecylamino)benzoate

A mixture of 8.0 g. of ethyl 4-(11-bromoundecylamino)benzoate, 4.0 g. of sodium methoxide and 5.3 g. of benzylthiol, and 100 ml. of methanol is stirred under reflux for 16 hours, cooled, diluted with 5% aqueous hydrochloric acid, and filtered. Recrystallization from ether-petroleum ether affords the product as a white solid. The procedure of Example 10 is used to convert the ester to 4-(11-benzylthioundecylamino)benzoic acid.

EXAMPLE 154

Preparation of ethyl 4-(6-azidohexadecylamino)benzoate

A solution of 6.4 g. of ethyl 4-(6-methanesulfonyloxyhexadecylamino)benzoate and 1.9 g. of sodium azide in 65 ml. of dimethylformamide is stirred at ambient temperature for 16 hours, poured into 200 ml. of water, and extracted with chloroform. The organic extract is washed with saturated sodium chloride solution, dried over sodium sulfate, and evaporated. Crystallization of the residue from hexane yields the product. The ester is hydrolyzed to 4-(6-azidohexadecylamino)benzoic acid using the procedure of Example 10.

EXAMPLE 155

Preparation of ethyl 4-(6-chlorohexadecylamino)benzoate

A solution of 10 g. of ethyl 4-(6-hydroxyhexadecylamino)benzoate and 2.4 ml. of pyridine in 50 ml. of chloroform is treated with 2.0 ml. of thionyl chloride, stirred under reflux for 1 hour, washed with 1 N hydrochloric acid and saturated aqueous sodium bicarbonate, dried over magnesium sulfate, and evaporated. The residue is crystallized from aqueous ethanol to yield the product as a white solid.

EXAMPLE 156

Preparation of ethyl 4-[11-(n-butylsulfinyl)undecylamino]benzoic acid

A solution of 5.2 g. of 4-[11-(n-butylthio)undecylamino]benzoic acid in 35 ml. of acetone and 20 ml. of tetrahydrofuran is treated with a solution of 3.7 g. of sodium metaperiodate in 3.5 ml. of water and 20 ml. of tetrahydrofuran and the mixture is stirred under reflux for 2 hours and then filtered. The filtrate is extracted with saturated aqueous sodium chloride solution, dried over magnesium sulfate, and evaporated. Crystallization from acetone-chloroform affords the product as a white solid.

EXAMPLE 157

Preparation of 4-[11-(n-butylsulfonyl)undecylamino]benzoic acid

A mixture of 3.8 g. of 4-[11-(n-butylthio)undecylamino]benzoic acid and 11 g. of sodium metaperiodate in 50 ml. of water and 200 ml. of methanol is stirred under reflux for 24 hours and filtered while hot. The filtrate was allowed to cool and then extracted with methylene chloride. The extract is dried over magnesium sulfate and evaporated to yield a solid. Recrystallization from acetone-chloroform affords the product as a white solid.

EXAMPLE 158

Preparation of ethyl 4-(3-oxotetradecylamino)benzoate

A solution of 1.8 g. of ethyl 4-(3-hydroxytetradecylamino)benzoate in 10 ml. of methylene chloride is added slowly to a stirred solution of 3.0 g. of chromium trioxide and 5.0 ml. of pyridine in 150 ml. of methylene chloride at ambient temperature and the mixture is stirred for 15 minutes. The supernatant liquid is decanted, washed with 1 N sodium hydroxide solution and 1 N hydrochloric acid, dried over magnesium sulfate, and evaporated. Crystallization of the residue from ether-petroleum ether yields the product as a white solid. Oxidation of the corresponding benzoic acid by this procedure affords 4-(3-oxotetradecylamino)benzoic acid.

EXAMPLE 159

Preparation of ethyl 4-(6-hydroxyhexadecylamino)benzoate

A suspension of 10 g. of ethyl 4-(6-oxohexadecylamino)benzoate and 2.8 g. of sodium borohydride in 250 ml. of ethanol is stirred at ambient temperature for 3 hours, acidified with glacial acetic acid, and poured into water. The solid is collected by filtration, dried, and recrystallized from hexane to yield the product as a white solid. Alkaline hydrolysis of this ester by the method of Example 10 affords 4-(6-hydroxyhexadecylamino)benzoic acid.

EXAMPLE 160

Preparation of 4-(6-oximinohexadecylamino)benzoic acid

A mixture of 1.0 g. of ethyl 4-(6-oxohexadecylamino)benzoate, 207 mg. of hydroxylamine hydrochloride, 244 mg. of sodium acetate and 20 ml. of 95% ethanol is stirred under reflux for 3 hours and filtered. The filtrate is evaporated and a methylene chloride solution of the residue is washed with water, dried over magnesium sulfate, and evaporated to yield ethyl 4-(6-oximinohexadecylamino)benzoate as a white solid.

A solution of the ethyl 4-(6-oximinohexadecylamino)benzoate, 1.0 g. of potassium hydroxide and 15 ml. of ethanol in 15 ml. of water is stirred under reflux for 2 hours, evaporated, and then treated with 15 ml. of water and 2.3 ml. of concentrated hydrochloric acid. The mixture is extracted with methylene chloride and the dried extract is evaporated. Crystallization from ethanol-water affords the product as a white solid.

EXAMPLE 161

Preparation of ethyl 4-(11-anilinoundecylamino)benzoate

A solution of 6.0 g. of ethyl 4-(11-bromoundecylamino)benzoate and 3.0 g. of aniline in 15 ml. of hexamethylphosphoramide is stirred at 115° for 18 hours, cooled, diluted with water, and filtered. Recrystallization of the solid from ethanol yields the product as an off-white solid. The ester is hydrolyzed to 4-(11-anilinoundecylamino)benzoic acid by the method of Example 10.

EXAMPLE 162

Preparation of ethyl 4-(11-benzenesulfonamidoundecylamino)benzoate

A solution of 6.0 g. of ethyl 4-(11-bromoundecylamino)benzoate, 5.0 g. of benzenesulfonamide, and 2.0 g. of sodium hydride (50% suspension in mineral oil) in 25 ml. of hexamethylphosphoramide is stirred at 115° for 18 hours, cooled, diluted cautiously with water, and filtered. The solid is recrystallized from ethanol to yield the product as a white solid. This ester is converted to 4-(11-benzenesulfonamidoundecylamino)benzoic acid by the method of Example 10.

EXAMPLE 163

Preparation of 4-(11-bromoundecylamino)benzoic acid

Anhydrous hydrogen bromide is passed rapidly into a solution of 5 g. of 4-(10-undecenylamino)benzoic acid and 1 g. of dibenzoyl peroxide in 300 ml. of 1,2-dimethoxyethane for 1 hour. Partial evaporation of the solvent affords a crystalline solid which is separated by filtration and recrystallized from ether-petroleum ether to yield the product as a white solid.

TABLE IV

Benzoic acids, esters, and amides required for the preparation of the 4-aminophenyl compounds of the table are prepared from the appropriate starting materials by the methods of Examples 5-7, 10, 12-14, 59-69, 112-120 and 149-150. The 4-aminophenyl compounds of the table are prepared from these acids, esters and amides by the methods of Examples 151-162.

| Example No. | Method of Example | Product |
|---|---|---|
| 164 | 151 | 4-(16-Mercaptohexadecylamino)benzoic acid |
| 165 | 151 | 4-(2-Mercaptotetradecylamino)benzoic acid |
| 166 | 151 | Ethyl 4-(11-mercaptoundec-2-enylamino)benzoate |
| 167 | 151 | Ethyl 4-[10-mercapto-1-methyl-2-(2-propenyl)decylamino]benzoate |
| 168 | 152 | 4-[12-Mercapto-1-(n-butyl)dodec-3-enylamino]benzoic acid |
| 169 | 152 | 4-(16-Mercaptohexadec-4-ynylamino)benzoic acid |
| 170 | 152 | 4-[(3-Mercapto-2,6,6-trimethylcyclohexyl)methylamino]benzoic acid |
| 171 | 153 | N[4-(16-Methylthiohexadecylamino)benzoyl]pyrrolidine |
| 172 | 153 | 4-(16-Phenylthiohexadec-9-enylamino)-N-(2,3-dihydroxypropyl)benzamide |
| 173 | 153 | 4-(7-Benzylthio-3-methylheptylamino)benzoic acid |
| 174 | 154 | 4-(16-Azidohexadecylamino)benzoic aicd |
| 175 | 154 | 4-(14-Azidotetradecylamino)benzoic acid |
| 176 | 154 | 4-(2-Azidotetradecylamino)benzoic acid |
| 177 | 155 | Ethyl 4-[(3-chloro-2,2,4-trimethylcyclopentyl)methylamino]benzoate |
| 178 | 155 | Ethyl 4-(16-chlorohexadec-4-ynylamino)benzoate |
| 179 | 155 | Ethyl 4-(16-Chlorohexadec-7-enylamino)benzoate |
| 180 | 156 | 4-[11-(n-Butylsulfinyl)undec-2-enylamino]benzoic acid |
| 181 | 156 | 4-(16-Methylsulfinylhexadecylamino)benzoic acid |
| 182 | 156 | 4-(8-Benzylsulfinyloctylamino)benzoic acid |
| 183 | 156 | 4-(10-Phenylsulfinyldectyamino)benzoic acid |
| 184 | 156 | 4-(2-Methylsulfinyltetradecylamino)benzoic acid |
| 185 | 157 | 4-[11-(n-Butylsulfonyl)undec-2-enylamino]benzoic acid |
| 186 | 157 | 4-(16-Methylsulfonylhexadecylamino)benzoic acid |
| 187 | 157 | 4-(10-Phenylsulfonyldecylamino)benzoic acid |
| 188 | 158 | Ethyl 4-(3-oxododecylamino)benzoate |
| 189 | 158 | Ethyl 4-(3-oxodecylamino)benzoate |
| 190 | 159 | 4-(6-Hydroxyundecylamino)benzoic acid |
| 191 | 159 | 4-(3-hydroxyundecylamino)benzoic acid |
| 192 | 159 | 4-(6-Hydroxytetradecylamino)benzoic acid |
| 193 | 159 | 4-(11-Hydroxyhexadecylamino)benzoic acid |
| 194 | 160 | 4-(2-Oximinotetradecylamino)benzoic acid |
| 195 | 160 | 4-(3-Oximinodecylamino)benzoic acid |
| 196 | 161 | 4-[8-(4-Chlorophenylamino)octylamino]benzoic acid |
| 197 | 161 | 4-[10-(p-Tolylamino)decylamino]benzoic acid |
| 198 | 162 | 4-(16-Methanesulfonamidohaxadecylamino)benzoic acid |
| 199 | 162 | 4-(2-Methanesulfonamidotetradecylamino)benzoic acid |
| 200 | 162 | 4-(11-Benzenesulfonamidoundec-2-enylamino)benzoic acid |
| 201 | 162 | 4-(11-Benzamidoundecylamino)benzoic acid |
| 202 | 162 | 4-(16-Acetamidohexadec-4-ynylamino)benzoic acid |
| 203 | 163 | 4-(2-Acetamidotetradecylamino)benzoic acid |

I claim:
1. A compound of the formula:

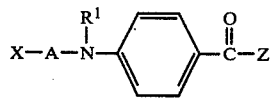

wherein

X is selected from the group consisting of chloro, bromo, and iodo;

A is selected from the group consisting of unbranched or branched alkylene groups optionally saturated or (mono- or poly-) unsaturated, represented by the formula $C_nH_{2(n-p)}$ with n being an integer from 7 to 18, inclusive, and p being an integer from 0 to 5, inclusive;

and Z is selected from the group consisting of (mono- or polyhydroxy)loweralkylamino, allylamino, propargylamino, 2-sulfoethylamino, (mono- or poly-carboxy)loweralkylamino, loweralkanoylamino, loweralkanesulfonylamino, loweralkanoylhydrazino, hydroxylamino, polymethyleneimino, and 4-carboethoxy- or 4-carboxythiazolidino;

wherein $R_1$ is hydrogen or is a group convertible in vivo thereinto such as, most notably, methyl, ethyl, carboxymethyl, acetyl, trifluoroacetyl, succinyl, 1-(sodium sulfo)loweralkyl, 1-(sodium sulfo)-polyhydroxyalkyl, and 1,3-bis(sodium sulfo)aralkyl;

and the pharmaceutically acceptable non-toxic acid-addition and cationic salts thereof.

2. A compound of the formula:

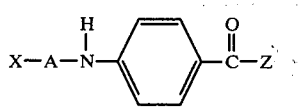

wherein
X is selected from the group consisting of chloro, bromo, and iodo;
A is selected from the group consisting of unbranched or branched saturated alkylene groups represented by the formula $C_nH_{2n}$ with n being an integer from 7 to 18, inclusive;
and Z is selected from the group consisting of (mono- or polyhydroxy)loweralkylamino, allylamino, propargylamino, 2-sulfoethylamino, (mono- or polycarboxy)loweralkylamino, loweralkanoylamino, loweralkanesulfonylamino, loweralkanoylhydrazino, hydroxylamino, polymethyleneimino, and 4-carboethoxy- or 4-carboxythiazolidino;
and the pharmaceutically acceptable non-toxic acid-addition and cationic salts thereof.

3. A compound of the formula:

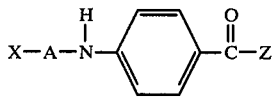

wherein
X is selected from the group consisting of chloro, bromo, and iodo;
A is selected from the group consisting of unbranched saturated alkylene groups, represented by the formula $C_nH_{2n}$ with n being an integer from 7 to 18, inclusive;
and Z is selected from the group consisting of (mono- or polyhydroxy)loweralkylamino, allylamino, propargylamino, 2-sulfoethylamino, (mono- or polycarboxy)loweralkylamino, loweralkanoylamino, loweralkanesulfonylamino, loweralkanoylhydrazino, hydroxylamino, polymethyleneimino, and 4-carboethoxy- or 4-carboxythiazolidino;
and the pharmaceutically acceptable non-toxic acid-addition and cationic salts thereof.

4. A compound of the formula:

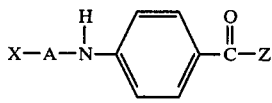

wherein
X is selected from the group consisting of chloro, bromo, and iodo;
A is selected from the group consisting of unbranched saturated alkylene groups, represented by the formula $C_nH_{2n}$ with n being an integer from 11 to 16, inclusive;
and Z is selected from the group consisting of (mono- or polyhydroxy)loweralkylamino, allylamino, propargylamino, 2-sulfoethylamino, (mono- or polycarboxy)loweralkylamino, loweralkanoylamino, loweralkanesulfonylamino, loweralkanoylhydrazino, hydroxylamino, polymethyleneimino, and 4-carboethoxy- or 4-carboxythiazolidino;
and the pharmaceutically acceptable non-toxic acid-addition and cationic salts thereof.

5. The compound 1-[4-(16-bromohexadecylamino)benzoyl]piperidine.

6. The compound 1-[4-(16-bromohexadecylamino)benzoyl]pyrrolidine.

* * * * *